(12) United States Patent
Fogelstrand et al.

(10) Patent No.: US 12,385,905 B2
(45) Date of Patent: Aug. 12, 2025

(54) METHOD FOR THE FORMATION AND USE OF AN IMMUNOLABELING COMPLEX

(71) Applicant: Kromnigon AB, Gothenburg (SE)

(72) Inventors: Per Fogelstrand, Mölndal (SE); Ulf Yrlid, Gothenburg (SE)

(73) Assignee: Kromnigon AB

( * ) Notice: Subject to any disclaimer, the term of this patent is extended or adjusted under 35 U.S.C. 154(b) by 653 days.

(21) Appl. No.: 17/667,153

(22) Filed: Feb. 8, 2022

(65) Prior Publication Data
US 2022/0155288 A1    May 19, 2022

Related U.S. Application Data

(63) Continuation of application No. 15/538,691, filed as application No. PCT/SE2016/050031 on Jan. 19, 2016, now abandoned.

(30) Foreign Application Priority Data

Jan. 21, 2015 (SE) .................................... 15500481
May 20, 2015 (SE) .................................... 15506405

(51) Int. Cl.
G01N 33/542 (2006.01)
G01N 33/53 (2006.01)
G01N 33/58 (2006.01)

(52) U.S. Cl.
CPC ....... *G01N 33/542* (2013.01); *G01N 33/5306* (2013.01); *G01N 33/58* (2013.01); *G01N 33/583* (2013.01)

(58) Field of Classification Search
CPC .. G01N 33/542; G01N 33/5306; G01N 33/58; G01N 33/583
See application file for complete search history.

(56) References Cited

U.S. PATENT DOCUMENTS

| | | |
|---|---|---|
| 2006/0286546 A1 | 12/2006 | Ramael et al. |
| 2007/0099248 A1 | 5/2007 | Ting et al. |
| 2008/0167243 A1 | 7/2008 | Schultz et al. |
| 2008/0286881 A1 | 11/2008 | Apel et al. |
| 2010/0285490 A1 | 11/2010 | Dees et al. |
| 2012/0171763 A1 | 7/2012 | Katayose |
| 2012/0214187 A1 | 8/2012 | Lees |
| 2014/0315761 A1 | 10/2014 | Beaman |

(Continued)

FOREIGN PATENT DOCUMENTS

| | | |
|---|---|---|
| EP | 0389301 A2 | 9/1990 |
| EP | 0389301 A3 | 9/1990 |
| EP | 2669296 A1 | 12/2013 |

(Continued)

OTHER PUBLICATIONS

Praul et al. (Biochemical and Biophysical Research Communication; 1998, 247, 312-314).*

(Continued)

*Primary Examiner* — Gailene Gabel
(74) *Attorney, Agent, or Firm* — RMCK Law Group, PLC (57) ABSTRACT

The present invention generally relates to method for forming an immunolabeling complex, the immunolabeling complex comprising a labeled monovalent biotin-binding composition. The invention also related to the use of the antibody-reporter molecule complex for detecting a target in a sample.

7 Claims, 3 Drawing Sheets

(56) References Cited

U.S. PATENT DOCUMENTS

| | | | |
|---|---|---|---|
| 2016/0258956 A1 | 9/2016 | Schwartz | |
| 2017/0045502 A1 | 2/2017 | Ohbayashi et al. | |

FOREIGN PATENT DOCUMENTS

| | | |
|---|---|---|
| EP | 1488000 B1 | 3/2014 |
| GB | 2098730 A | 11/1982 |
| SE | 1550041 A1 | 7/2016 |
| WO | 9727486 A1 | 7/1997 |
| WO | 2007096637 A1 | 8/2007 |
| WO | 2009032128 A1 | 3/2009 |
| WO | 2013038272 A2 | 3/2013 |
| WO | 2014163557 A1 | 10/2014 |
| WO | 2016118065 A1 | 7/2016 |

OTHER PUBLICATIONS

Sabharwarl et al. (Annals of Biomedical Engineering, 2009; vol. 37, No. 10, pp. 1967-1973).*
U.S. Appl. No. 15/538,691, filed Jun. 22, 2017, Fogelstrand et al.
U.S. Appl. No. 15/543,465, filed Jul. 13, 2017, Fogelstrand et al.
Anti-c-myc Antibody (2010, retrieve from http://www.aveslab.com/products/epitope-tag-and-gfp-antibodies/fluorescein-itc-labeled-anti-c-myc-antibodies/, 4 pages.
Carayanniotis, G., et al., "Adjuvant-independent immunization by immunotargeting antigens to MHC and non-MHC determinants in vivo", Molecular Immunology, vol. 28, No. 3, 1991, pp. 261-267.
Chinese Office Action for Chinese Application No. 2016800006512.6 mailed May 22, 2018 with English translation, 15 pages.
Communication Pursuant to Article 94(3) EPC dated Dec. 9, 2019 from European Patent Office for EP Application No. 16740471.4, 4 pages.
Corada, M. et al., "Monoclonal Antibodies Directed to Different Regions of Vascular Endothelial Cadherin Extracellular Domain Affect Adhesion and Clustering of the Protein and Modulate Endothelial Permeability," Blood, Mar. 15, 2001, vol. 97, No. 6, pp. 1679-1684.
European Search Report for EP Application No. 16740471.4 mailed May 7, 2018, 6 pages.
European Search Report for EP Application No. 16740472.2 mailed May 4, 2018, 7 pages.
Haugland, Rosaria P., "Antibody Conjugates for Cell Biology" in: "Current Protocols in Cell Biology" Supplement 6, (2000), pp. 16.5.1-16.5.22.
Hosokawa, K., et al., "Immunoassay on a power-free microchip with laminar flow-assisted dendritic amplification", Analytical Chemistry, 2007, vol. 79, No. 15, pp. 6000-6004.
Howarth, M. et al., "A monovalent streptavidin with a single femtomolar biotin binding site," Nature Methods, vol. 3, No. 4, Apr. 2006, pp. 267-273.
International Search Report and Written Opinion for International Application No. PCT/SE2016/050027 mailed Apr. 6, 2016, 12 pages.
International Search Report and Written Opinion for International Application No. PCT/SE2016/050031 mailed Apr. 5, 2016, 12 pages.
Lim, Kok Hong, et al., "Stable, high-affinity streptavidin monomer for protein labeling and monovalent biotin detection", Biotechnology and Bioengineering, vol. 110, No. 1, Jan. 1, 2013, pp. 57-67.
Padlan, E., "X-Ray Crystallography of Antibodies," Advances in Protein Chemistry, vol. 49, 1996, pp. 57-133.
Secondary Antibody Selection, 2002, https://www.ptglab.com/news/blog/secondary-antibody-selection, 4 pages.
Taylor, S. et al., "Monovalent Streptavidin that Senses Oligonucleotides", Angewandte Chemie International Edition, vol. 52, No. 21, May 17, 2013, 9 pages.
Vincent, P. et al., "A comparison of the binding of biotin and biotinylated macromolecular ligands to an anti-biotin monoclonal antibody and to streptavidin," Journal of Immunological Methods, vol. 165, Issue 2, Oct. 15, 1993, 2 pages.
Wiedorn, K.H. et al., "EnVision+, a New Dextran Polymer-based Signal Enhancement Technique for In Situ Hybridization (ISH)," The Journal of Histochemistry & Cytochemistry, vol. 49(9), 2001, pp. 1067-1071.
Park, S.H. et al., "Generation and application of new rat monoclonal antibodies against synthetic FLAG and OLLAS tags for improved immunodetection," Journal of Immunological Methods, vol. 331, Feb. 2008, pp. 27-38.
Kuby, J., "Immunology," W.H. Freeman Company, 1992, p. 125.
Wolfe, S.L., "Molecular and Cellular Biology," Academic Press Dictionary of Science and Technology, Programmed Genetic Rearrangements in the Production of Antibodies, Chapter 19, 1993, pp. 790-793.

* cited by examiner

METHOD FOR THE FORMATION AND USE OF AN IMMUNOLABELING COMPLEX

CROSS-REFERENCE TO RELATED APPLICATIONS

This application is a continuation of U.S. patent application Ser. No. 15/538,691, filed Jun. 22, 2017, which is a 371 U.S. National Stage of International Application No. PCT/SE2016/050031, filed Jan. 19, 2016, which claims priority to Swedish Application No. 1550048-1, filed on Jan. 21, 2015 and Swedish Application No. 1550640-5, filed on May 20, 2015. The disclosures of each of the above applications are incorporated herein by reference in their entirety.

TECHNICAL FIELD

The present invention generally relates to method for forming an immunolabeling complex, the immunolabeling complex comprising a labeled monovalent biotin-binding composition. The invention also related to the use of the antibody-reporter molecule complex for detecting a target in a sample.

BACKGROUND OF THE INVENTION

In immunolabeling, antibodies are used for detection of molecules in biological and non-biological samples. Antibodies are immunoglobulin (Ig) proteins that bind with high specificity through its antigen-binding site to an antigen (target molecule). Typically the target molecule is a protein, but can be any immunogenic agent such as polysaccharides, lipids, toxins etc. The part of the target molecule to which the antibody binds is called epitope. Antibodies used for immunolabeling can be polyclonal or monoclonal. Polyclonal antibodies are a heterogeneous mix of antibodies that recognize several epitopes of one target molecule, while monoclonal antibodies show specificity for a single epitope. In general, monoclonal antibodies render more specific immunolabeling signals.

Immunolabeling can either be direct or indirect. The direct method is a one-step labeling method and involves a primary antibody that is labeled with a reporter molecule. The reporter molecule (label) is a molecule that can generate a signal, such as an enzyme or fluorochrome (further described below). When the labeled primary antibody is added to a sample it binds and reveals the location and/or amount of the target molecules. Since the direct method utilizes only one incubation step with the sample it is simple and rapid.

The indirect method is a two-step labeling method that results in signal amplification. It involves a primary antibody (first step) that binds to the target molecules in the sample and a labeled secondary antibody (second step) that binds to the bound primary antibody. Since several labeled secondary antibody molecules bind to each primary antibody molecule, the reporter signal will be amplified compared to the direct method. However, the indirect method requires one extra incubation step and the secondary antibody needs to be carefully adjusted to the primary antibody. The secondary antibody is usually raised against the Ig class of the animal species in which the primary antibody was raised. For example if the primary antibody is a mouse IgG antibody, the secondary antibody is an anti-mouse IgG antibody. If the primary antibody is a rabbit IgG, then the secondary antibody is an anti-rabbit IgG etc.

Streptavidin (or other derivates of avidin) can also be used in immunolabeling with the indirect method by using biotinylated antibodies. Biotinylated antibodies are antibodies that have been conjugated with biotin molecules (usually 3-10 biotin molecules/antibody molecules). Streptavidin binds strongly to biotin, and can thus be used to as a secondary reagent to biotinylated antibodies. In some applications when the nature of the sample is plastic, such as the membrane of living cells, regular streptavidin can cause antibody aggregation. This is because each streptavidin molecule has four biotin-binding sites and when added as a secondary reagent it can bind several biotinylated antibodies that are 'floating around' in the sample. To avoid this phenomenon, a monovalent form of streptavidin has been engineered (Howarth M et al, Nature methods, 2006). Monovalent streptavidin has only one biotin-binding site. Consequently it can be used as a secondary reagent to visualize biotinylated antibodies that are bound to target molecules in membranes of living cells without the risk of antibody aggregation.

The reporter molecules used in immunolabeling vary depending on the nature of the detection method. They are directly attached (conjugated) to the primary antibody (direct method) or to the secondary antibody/streptavidin (indirect method). The reporter molecules are conjugated to antibodies through a chemical reaction that results in a covalent bond between the reporter molecule and the antibody. Hence, the reporter molecule and the antibody become one unit. Usually, several reporter molecules are conjugated to each antibody molecule. The most common reporter molecules are enzymes for chromogenic detection or fluorochromes for fluorescence signals. Other examples are particles (e.g. gold particles, quantum dots), phosphorescent compounds (e.g. carbocyanide dyes), radioactive compounds (e.g. 3H or 32P labeled molecules) and transition metals (for mass spectrometry). For some classes of reporter molecules, such as fluorochromes and transition metals, several signals can simultaneously be separated and analyzed within one sample. This means that several different target molecules can be immunolabeled and detected simultaneously within one sample. This multi-immunolabeling technique is for example commonly used by fluorescence microscopy and flow cytometry.

Since the choice of reporter elements varies between experiments/applications it is highly desirable to switch reporter molecules on the antibody. However, in the direct method the reporter molecule and the antibody are firmly attach to each other as one unit. Thus, a new reporter molecule-antibody unit has to be obtained if a new reporter molecule is preferred, instead of just changing the reporter molecule.

In this sense, the indirect method is more flexible as the reporter molecule is attached to the secondary antibody. The reporter molecule can therefore be altered by switching between secondary antibodies with different reporter molecules. However, as mentioned above, this requires an extra incubation step with the sample. Furthermore, the use of secondary antibodies causes problems with cross-binding of antibodies, i.e. the secondary antibodies do not only bind to the primary antibodies they are intended to bind, but in addition bind to other antibodies that is not intended. These other antibodies can be 1) endogenous antibodies within the tissue, 2) other primary antibodies, and 3) other secondary antibodies. The problem arises from that the secondary antibody binds all antibodies derived from the same animal species. Hence, each primary antibody needs to be of a different antibody class (animal species), and each secondary antibody must selectively recognize only one of those classes. In addition, none of the secondary antibodies can be of an antibody class that is recognized by any of the other secondary antibodies. This is a well-known problem in the art, and greatly limits the number of antibodies that can be combined in multi-immunolabeling.

An alternative approach is to pre-form a complex between the primary antibody and the secondary antibody and then use this complex for the direct immunolabeling method. However, mixing primary antibodies with secondary antibodies results in antibody aggregates, since antibodies have two epitope-binding sites. To avoid formation of antibody aggregation, monovalent secondary antibodies can be used. However, forming a complex between antibodies requires that the secondary antibody is adjusted to the animal species of each primary antibody. Moreover, since the binding between antibodies are not that strong, the complex is instable and a blocking reagent is needed that sequester free reactive secondary antibodies. The blocking reagent (part of an antibody that lack epitope binding sites) also needs to be adjusted so that it is derived from the same animal species as the primary antibody.

Although there are some methods, based on secondary antibodies, that provide some flexibility to switch between reporter molecules, directly labeled antibodies are still preferred when using the direct immunolabeling method. Thus, a robust and simple method to attach reporter molecules to primary antibodies for the use of the direct immunolabeling method is highly desirable.

SUMMARY OF THE INVENTION

The invention relates to a method of connecting reporter elements to antibodies using biotin 'click chemistry'. The reporter molecule unit consists of a monovalent form of a biotin-binding composition to which one or several reporter elements are attached. The antibody unit consists of a biotinylated antibody. The two separate units can easily be connected by click chemistry into an immunolabeling complex that contain both the antibody function and reporter element function, hence, the same functions as directly conjugated antibodies.

Advantages with the invention include that the antibody function and the reporter element function are separate units from the start and that they can form a very stable complex by simple mixing. Furthermore, the method is independent of the antibody class of the antibodies. Together, this creates a flexible and simple system to attach a variety of reporter elements to antibodies. Importantly, the labeled antibodies can subsequently be used for the direct immunolabeling method (one step).

In addition, advantages of using click chemistry over conventional conjugation chemistry includes that it is fast, no extra reactive chemicals are needed, no by-products are formed (the product is ready to use), and the amounts and concentrations of the reagents can be altered from very low to very high. These features make the inventive method suitable for small scale conjugation 'at the lab bench' to large scale conjugation for distribution.

According to an aspect of the invention, the above is at least partly achieved by a method for forming a (stable) immunolabeling complex, wherein the method comprises selecting a first biotinylated primary antibody, selecting a first monovalent biotin-binding composition labeled with a first reporter element, and mixing, in a reaction vessel, the first biotinylated primary antibody with the first labeled monovalent biotin-binding composition.

As discussed above, it is possible to use biotinylated primary antibodies and regular streptavidin to achieve amplification during immunolabeling of a sample. However, such an approach must be performed sequentially in two steps because regular streptavidin contains four biotin-binding sites and thus can only be used on biotinylated antibodies that are bound to a solid phase (such as a fixed tissue sample). Adding regular streptavidin to biotinylated antibodies in a liquid phase has the very undesirable effect of rapid aggregation into big antibody complexes. However, in accordance to the invention, a monovalent biotin-binding composition is instead used, with only one functional binding site for biotin, which thereby avoids antibody aggregations during the mixing step in a liquid phase (in the reaction vessel). Thus, the monovalent biotin-binding composition is not used as a secondary labeling reagent, but as a carrier of reporter molecules to form a stable complex with biotinylated antibodies to be used as directly conjugated antibodies. It should be understood that the sample is different from the first biotinylated primary antibody.

In addition, the method allows more reporter element molecules to be connected to each antibody molecule than possible for direct conjugation of reporter elements to antibodies. Hence, the method can be used to generate stronger signals than directly conjugated antibodies. Furthermore, when using monovalent biotin-binding composition, such as monovalent streptavidin, to form an immunolabeling complex, new technical parameters become important. Care must be taken to retain the binding function of the antibody (its epitope-binding site). Overloading the antibody with monovalent streptavidin can sterically block its epitope-binding site. Thus, an antibody cannot be regarded as any protein, but must be regarded as a protein with a special functional quality. To minimize steric hindrance of its epitope-binding site, the molecular ratio between monovalent streptavidin and the antibody must be carefully chosen. Furthermore, even at an optimal monovalent streptavidin-to-antibody ratio, the rapid binding reaction between monovalent streptavidin and the biotinylated antibody causes an unexpected phenomenon for immunolabeling techniques. Since the reaction is rapid, the first biotinylated antibodies that come in close contact with streptavidin in the liquid mixture will be fully loaded with streptavidin, leading to a shortage of streptavidin molecules for the remaining antibodies in the mixture.

Consequently, the mixture will contain a heterogeneous population of immunolabeling complexes, where some antibodies are overloaded with monovalent streptavidin while other antibodies contain no or few monovalent streptavidin. When this heterogeneous mixture is used for immunolabeling of a sample, the antibodies with a low monovalent streptavidin cargo will have an advantage to bind the epitopes in the sample because of 1) less steric hindrance of the epitope binding site of the antibody and 2) the smaller size of the monovalent streptavidin-antibody complex. Hence, antibodies with low or no monovalent streptavidin cargo will preferentially bind to the target molecules (epitopes) in the sample, leading to a weak immunolabeling signal. Since a bright signal is key for immunolabeling techniques, an even distribution of monovalent streptavidin and a correct monovalent streptavidin-to-antibody ratio is crucial for the immunolabeling complex. In contrast, when using regular streptavidin for the indirect method, streptavidin can be added in surplus without any concerns of altering the binding function of the antibodies or the streptavidin distribution, since the biotinylated antibodies are already bound to a solid surface in the sample (further discussed below).

To facilitate an even distribution of monovalent streptavidin between antibody molecules, variants of monovalent biotin-binding compositions with slower on-rate binding to biotin may be used, such as traptavidin, which binds 10 times slower to biotin than streptavidin (Nat Methods. 2010,7(5):391-3). It is also possible to change conditions in mixing, temperatures, viscosities etc. to achieve a more even distribution of monovalent streptavidin onto biotinylated antibodies.

As mentioned earlier, it is possible to use biotinylated primary antibodies and regular streptavidin for immunolabeling of a sample. However, such an approach must be performed sequentially in two steps because regular streptavidin contains four biotin-binding sites and thus can only be used on biotinylated antibodies that are bound to a solid phase (such as a fixed tissue sample). Adding regular streptavidin to biotinylated antibodies in a liquid phase has the very undesirable effect of rapid aggregation into big antibody complexes.

Consequently, regular streptavidin can only be used for the indirect immunolabeling method, similar to a secondary antibody, and not for the direct method.

As understood from the above, the immunolabeling complex is preferably subsequently used in contacting with a sample. However, the immunolabeling complex may in itself be provided as a separate component provided to e.g. researchers, where the researchers will perform the step of using the immunolabeling complex for immunolabeling of a sample. In a possible embodiment of the invention, the biotinylated antibody and the monovalent biotin-binding composition are provided as two separate units with instructions how to form the immunolabeling complex to be used in contacting with the sample. Accordingly, selecting the first biotinylated primary antibody and selecting the first monovalent biotin-binding composition may be performed separated from mixing the first biotinylated primary antibody with the first labeled monovalent biotin-binding composition. Possibly, the mixing is performed at a separate location from the selection of the first biotinylated primary antibody and the first monovalent biotin-binding composition.

In accordance to the invention, the expression "monovalent biotin-binding composition" is to be interpreted broadly. For example, the monovalent biotin-binding composition may be based on at least one of streptavidin, avidin, traptavidin, captavidin, tamavidin, bradavidin, neutravidin, and rhizavidin, etc., or any further developed or found equivalent molecule or combinations of molecules having an appropriate biotin-binding configuration.

In a possible embodiment of the invention the monovalent biotin-binding composition comprises monovalent streptavidin (or a derivate of streptavidin). There exist different methods for engineering monovalent streptavidin. The streptavidin molecule is a tetramer consisting of four equal subunits, where each subunit has a binding site for biotin. Monovalent streptavidin can be achieved by generating monomers of streptavidin, i.e. single subunits, forming monomeric streptavidin. However, monomeric streptavidin has much lower binding affinity than tetrameric streptavidin, since part of its biotin binding site comes from a neighboring subunit. Monovalent tetrameric streptavidin with remained high binding affinity for biotin can be generated by at least two different approaches. First, by assembling streptavidin that consists of one functional subunit (alive subunit) and three mutated subunits that lack affinity for biotin (dead subunits) (Nature Methods. 2006, 4:267-73). Second, by treating tetrameric streptavidin with trisbiotinylated oligonucleotide that blocks three of the four biotin-binding sites on streptavidin (Angew Chem Int Ed Engl. 2013, 52(21): 5509-12). It should be understood that any future design of monovalent biotin-binding molecules could be possible and is to be considered equivalent to and comprised within the generic term monovalent streptavidin composition. However, when using monovalent streptavidin for the monovalent biotin-binding composition, the use of monovalent tetrameric streptavidin is currently preferred.

It should be understood that streptavidin binds extremely tight to biotin, and the present method uses a biotinylated primary antibody to form a complex with streptavidin. Biotinylated antibodies are antibodies that are covalently conjugated with several biotin molecules, usually 3-10 biotin molecules per antibody. Because several streptavidin molecules bind to each biotinylated antibody, signal amplification may be achieved. The streptavidin-biotin binding is the strongest known non-covalent binding, and it is 1000-1000000 times stronger than the binding that can be generated from an antibody. Thus, the complex between biotinylated primary antibodies and streptavidin results in a much more stable complex than the binding between primary and secondary antibodies.

It is preferred (but optional) to further comprise adding a blocking agent to block unbound portions of the monovalent of the monovalent biotin binding composition after the first immunolabeling complex has been formed. The blocking agent is preferably free biotin. The addition of the blocking agent will make any surplus e.g. monovalent streptavidin inreactive, thereby reducing the risk of an unwanted reaction between surplus monovalent streptavidin and a further biotinylated primary antibody. It may as an alternative be possible to reduce this unwanted reaction by the introduction of a careful titration step and allowing the mixing step (the reaction between the biotinylated primary antibody and the monovalent streptavidin composition) to be long "enough".

The reporter element may in one embodiment be selected from a group comprising a fluorochrome, an enzyme, a peptide, quantum dots, and a transition metal. Some of the disclosed reporter elements are known to the skilled person, it should however be understood that other/future reporter elements may equally be used in relation to the invention.

For example, using a fluorochrome as a reporter element in relation to "regular" tetravalent streptavidin is well known to the skilled person. Labeling of regular streptavidin with a range of different molecules, including fluorochromes, proteins, peptides, oligonucleotides, is similarly a well-known process that in a similar manner may be used for labeling e.g. monovalent streptavidin for forming the first monovalent streptavidin composition.

In a preferred embodiment of the invention the ratio between the first monovalent biotin binding composition and the first biotinylated primary antibody is selected such that the risk of the first monovalent biotin binding composition blocking active biding sites of the first biotinylated primary antibody is reduced.

On the other hand, if too few molecules of the monovalent biotin binding composition are attached to each antibody molecule there will instead be a weak detection signal. However, the signal can be further enhanced through several different means. First, the monovalent biotin-binding composition can be modified so that e.g. more fluorochrome molecules can be attached (conjugated) to it. This can be obtained either by making the monovalent biotin-binding composition larger, i.e. increase the surface available for fluorochrome conjugation, or increasing the density of available conjugation sites for fluorochromes, i.e. increase the number of chemical groups that can be used for e.g fluorochrome conjugation, such as —$NH_2$ groups or aldehydes. For example, in regards to the use of monovalent streptavidin, the latter can be obtained by adding tags rich in fluorochrome conjugation sites, such as lysine rich tags. The tags can be incorporated in the amino acid sequence of streptavidin or chemically added in a separate step. It is also possible to chemically attach macromolecules that comprise a plurality of molecules of a reporter element to the monovalent biotin-binding composition. Such macromolecules can be polymers, for example dextran and polyethylene glycol (PEG).

Another strategy to enhance the signal is to add a separate enhancer step. For example, in regards to the use of monovalent streptavidin, the streptavidin can be labeled with an antigen tag that is recognized by antibodies that are used to enhance the signal. The antigen tag can be incorporated in the amino acid sequence of streptavidin or chemically added in a separate subsequent step. The antibodies used for the antigen detection (amplification step) can either be directly conjugated with a reporter molecule, such as a fluorochrome, or conjugated with another second antigen that is recognized by a second antibody that is conjugated with a reporter molecule. This concept is further disclosed in SE1550041-6 by the applicant, which content is fully incorporated by reference. The streptavidin may also be labeled with oligonucleotide probes that are recognized by Padlock probes for rolling-circle amplification (Nature Methods. 2006, 3:725-727) or big complexes that contain both antisense probes and reporter elements, such as dextran-based complexes with attached antisense probes and fluorochromes. Thus, by adding downstream amplification steps the number of monovalent biotin-binding molecules bound to each biotinylated antibody can be kept low, which minimizes the risk of sterical hindrance of the antibody's antigen-binding site.

In accordance to the invention the inventive immunolabeling complex is used for detecting a target in a sample, the sample being a biological sample or non-biological samples. Thus, in an embodiment of the invention the first immunolabeling complex as discussed above is contacted with the sample, and incubated for a time sufficient to permit the first immunolabeling complex to selectively bind to the target, and then the immunolabeling complex is detected by development of a signal from the label, for example illumination of the sample under a microscope to detect a light from a fluorochrome. In such an embodiment the reporter element is preferably a fluorochrome.

In a preferred embodiment of the invention a second immunolabeling complex formed as discussed above is also contacted with the sample, and the sample is in a similar manner incubated for a time sufficient to permit the second immunolabeling complex to selectively bind to the target. In the preferred embodiment, the second immunolabeling complex comprises a second biotinylated primary antibody mixed with a second monovalent biotin binding composition, the second biotinylated primary antibody being different from the first biotinylated primary antibody, and the second monovalent biotin binding composition being labeled with a second reporter molecule being different from the first reporter molecule. The second immunolabeling complex is preferentially added to the sample together with the first immunolabeling complex.

The method can be used alone or in combination with any other immunolabeling method, for example in combination with directly conjugated primary antibodies (direct method) or in combination with primary antibody+labeled secondary antibody (two-step method), or in combination with biotinylated primary antibody+labeled regular streptavidin (two-step method). The latter requires that the present method is added after labeling with biotinylated primary antibody+labeled regular streptavidin, and that the labeled sample is blocked with free biotin before adding the immunolabeling complexes of the present method. Alternatively, monovalent streptavidin can be used in the two-step method to avoid the need for the biotin blocking step before adding the immunolabeling complexes of the present method.

According to further aspect of the invention there is provided a kit of immunolabeling complexes, comprising a first and a second immunolabeling complex formed in accordance to the above discussion, wherein the second immunolabeling complex comprising a second biotinylated primary antibody mixed with a second monovalent biotin-binding composition, the second biotinylated primary antibody being different from the first biotinylated primary antibody, and the second monovalent biotin binding composition being labeled with a second reporter molecule being different from the first reporter molecule.

As will be understood by the skilled person, the invention will for example allow for the possibility to have the freedom of labeling, in an embodiment, four primary antibodies, independently if they are made in mouse, rat, rabbit or goat, and for this you only need a kit of four monovalent streptavidin labeled with four different fluorochromes. The equivalent kit with monovalent secondary antibodies requires four different secondary antibodies (anti-mouse, anti-rat, anti-rabbit and anti-goat), each labeled with the four different fluorochromes, which in total is 16 different monovalent secondary antibodies.

Furthermore, while the inventive implementation using monovalent streptavidin only needs free biotin as blocking reagent, the monovalent secondary antibodies need four different blocking reagents (one for each animal species). Thus, a kit of five components of monovalent streptavidin (four labeled monovalent streptavidin+one blocking reagent), requires a kit of 20 components for a corresponding kit of monovalent secondary antibodies (16 labeled monovalent antibodies+four blocking reagents).

According to a still further aspect of the invention there is provided a kit of an immunolabeling complex and an enhancer step, comprising an immunolabeling complex formed in accordance to the above discussion, and at least one first enhancer component, wherein the monovalent biotin-binding composition comprises a first set of at least one of antigens and oligonucleotides that are recognized by the first enhancer component, and the first enhancer component is conjugated with reporter elements, or the first enhancer component is conjugated with a second set of at least one of antigens and oligonucleotide that are recognized by a second enhancer component that is conjugated with reporter elements, wherein the second set is different from the first set. The enhancer components are preferably formed as discussed above.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Figure 1A:
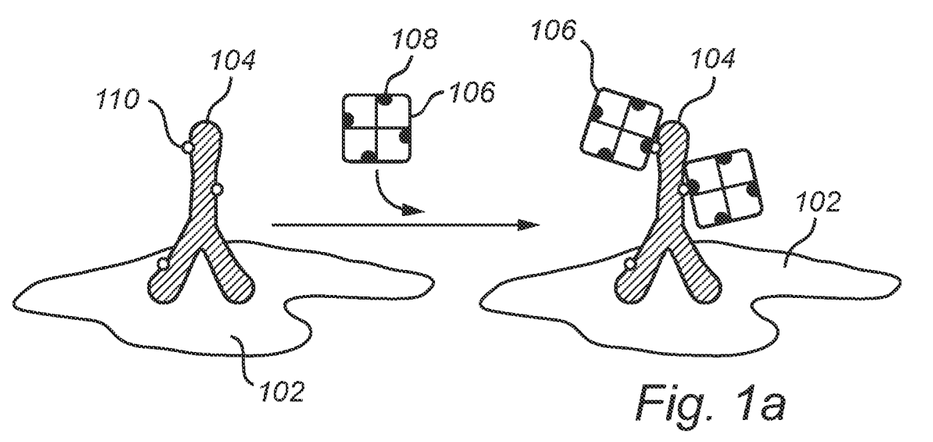
FIGS. 1a and 1b shows an example of a biological sample which has been incubated with biotinylated antibodies.

Referring now to the drawings and to FIG. 1a in particular, showing a standard immunolabeling procedure using regular streptavidin. Regular streptavidin can only be used in the indirect two step method, and it can only be used for one biotinylated antibody. There is on the left hand side depicted a biological sample 102 which has been incubated with a biotinylated antibody 104. The biotinylated antibody 104 binds to a first target antigen in the biological sample 102, and has been specifically selected for allowing subsequent detection/analysis in e.g. a subsequent immunofluorescence process. For allowing detection of the first target antigen, the sample 102 with the bound biotinylated antibody 104 is incubated with labeled streptavidin 106 (right hand side of FIG. 1a). The labeling component provided with the streptavidin is a reporter element, such as for example a fluorochrome conjugated with streptavidin, thereby forming the labeled streptavidin 106. Other types of reporter elements are possible. The selection of reporter element is done based on the application at hand. In FIG. 1a, a biotin-binding site of the labeled streptavidin 106 is indicated as a "black circle" denoted as 108. Similarly, a biotin molecule 110 is indicated as a "white circle" at the biotinylated antibody 104, where the biotin molecule 110 is conjugated to the antibody 104

Figure 1B:
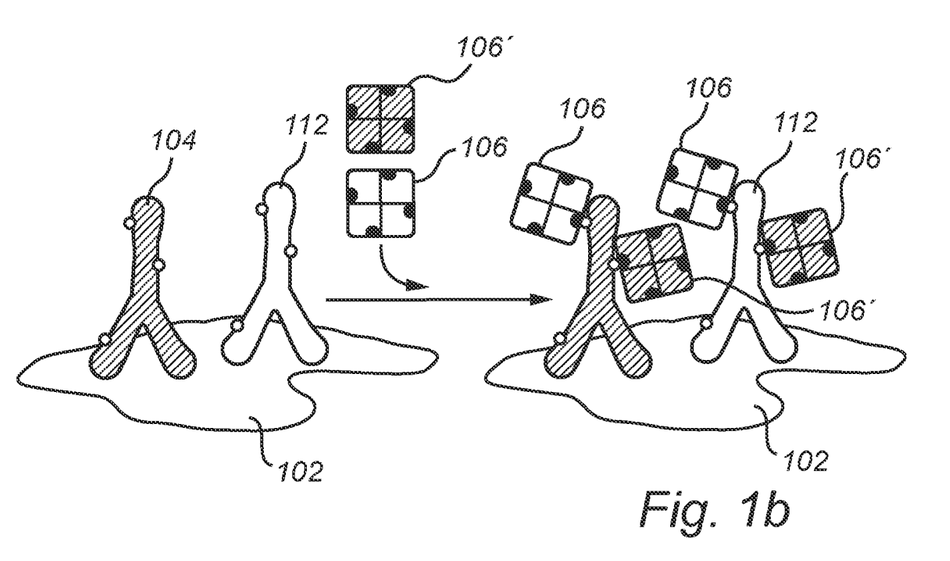

Streptavidin can only be used for detection of one biotinylated antibody in the indirect immunolabeling method (two-step). If the sample is incubated with a first biotinylated antibody 104 recognizing a first target antigen together with a second biotinylated antibody 112 recognizing a second target antigen, followed by incubation with two (different) labeled streptavidin 106 and 106', both antibodies 104 and 112 will be labeled by both labeled streptavidins 106 and 106', FIG. 1b. Hence, in this two-step method each biotinylated antibody will generate a mix of two signals, for example emit light at two different colors, if the labels are fluorochromes.

Figure 2A:
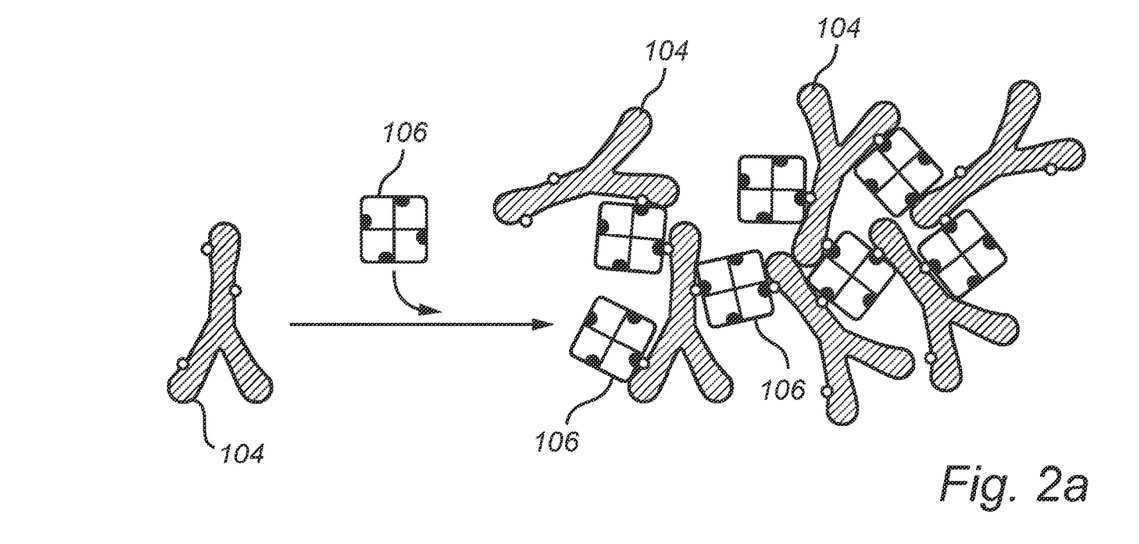
FIGS. 2a and 2b illustrates a pre-incubation process in a liquid phase involving regular tetravalent streptavidin, and monovalent streptavidin.

One could possibly believe that this problem could be solved by pre-labeling the first biotinylated antibody 104 with the first labeled streptavidin 106 and the second biotinylated antibody 112 with the second labeled streptavidin 106', before adding them to the sample 102. However, when using "regular" streptavidin having four biotin-binding sites (tetravalent), an aggregate will be formed because each streptavidin molecule 106 will bind to more than one biotinylated antibody molecule 104, and each biotinylated antibody 104 will bind to more than one streptavidin molecule 106 as is shown in FIG. 2a and as has been further discussed above.

Figure 2B:
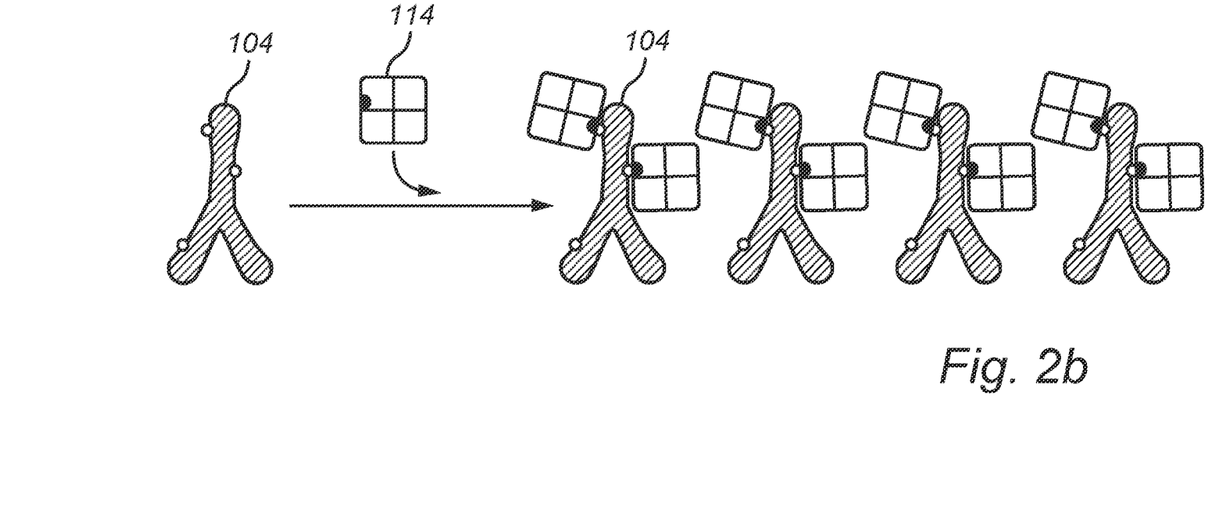

However, in accordance to the invention, a monovalent biotin-binding composition is used, having only a single biotin-binding site. As is shown in FIG. 2b, using labeled monovalent streptavidin 106' in a pre-incubation process with the first primary antibody 104 in a liquid phase will enable forming an immunolabeling complex between the biotinylated antibody 104 and the labeled monovalent streptavidin 114 without aggregation, by means of a click chemistry process. Advantages of using click chemistry over conventional conjugation chemistry includes that it is fast, no extra reactive chemicals are needed, no by-products are formed (the product is ready to use), and the amounts and concentrations of the reagents can be altered from very low to very high. These features make the inventive method suitable for small scale conjugation 'at the lab bench' to large scale conjugation for distribution. This pre-incubation step will further enable formation of multiple immunolabeling complexes between biotinylated antibodies and monovalent streptavidin; such that a large plurality of different primary antibodies 104 each conjugated with labeled monovalent streptavidin 114 could be formed (i.e. no aggregates are formed as compared to FIG. 2a).

Figure 3:
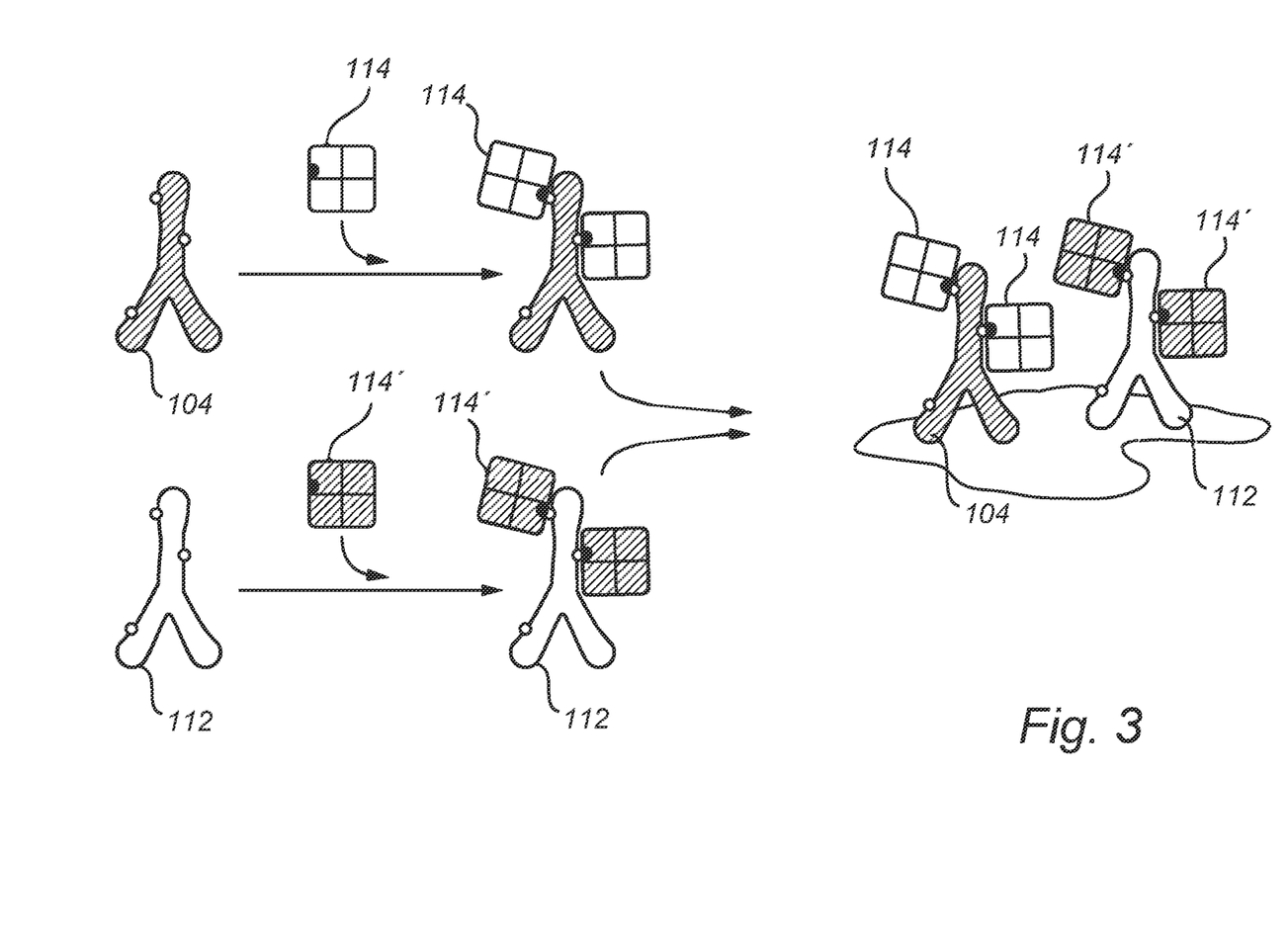
FIG. 3 exemplifies a multi-immunolabeling process according to an embodiment of the invention, the pre-incubation process making use of a monovalent biotin-binding molecule.

As the monovalent streptavidin may be labeled with not only a single type of reporter molecule, but rather with a large plurality of different reporter molecules, e.g. different fluorochromes being active within different wavelength ranges, it may in accordance to the invention be possible to create a set comprising a plurality of different primary antibodies (e.g. the first 104 and the second 112 primary antibody as is shown in FIG. 3, each of the primary antibodies targeting a different antigen comprised with the biological sample 102), each of the primary antibody to be (separately) pre-incubated with a differently labeled monovalent streptavidin, such as labeled monovalent streptavidin 114 and 114'. This is possible because the immunolabeling complexes can be used for the direct immunolabeling method (1-step).

A first primary antibody 104 may thus be pre-incubated with a first monovalent streptavidin composition 114 forming a first immunolabeling complex in a liquid phase, and a second primary antibody 112 may be pre-incubated with a second monovalent streptavidin composition 114' forming a second immunolabeling complex in a liquid phase. As the first 114 and the second 114' monovalent streptavidin composition advantageously are labeled with different types of reporter elements, such as for example being labeled with different types of fluorochromes, it will in a subsequent analysis process be possible to separately detect/analyze a first and a second target antigen in the sample by incubating the sample with the first and the second immunolabeling complexes.

It should be noted that it is desirable to add a blocking agent to block unbound monovalent streptavidin after the pre-incubation process for each of the first 104 and the second 112 primary antibodies. Such a blocking agent is preferably free biotin. The addition of the blocking agent will make any surplus monovalent streptavidin inreactive, thereby reducing the risk of an unwanted reaction between the surplus monovalent streptavidin and a further biotinylated primary antibody, e.g. the first 104 vs. the second 112 primary antibody.

In summary, the present invention relates to a method for attaching reporter molecules to an antibody by using biotin click chemistry. This is alleviated by forming an immunolabeling complex, wherein the method comprises selecting a first biotinylated primary antibody, selecting a first monovalent biotin-binding composition labeled with a first reporter element, and mixing in a liquid phase in a reaction vessel, the first biotinylated primary antibody with the first labeled monovalent biotin-binding composition.

In accordance to the invention, a monovalent biotin-binding composition with only one functional binding site for biotin is used, thereby avoiding antibody aggregations during the mixing step in a liquid phase. As a comparison, e.g. regular streptavidin has four binding sites for biotin, which causes rapid aggregation if premixed with biotinylated antibodies in a liquid phase.

Advantages with the invention include that only one labeling reagent (e.g. monovalent streptavidin) and one blocking reagent (biotin) is needed. This is because the present invention is completely antibody-class independent. Other comparable methods are typically based on secondary antibodies, and hence dependent on adjusting the secondary antibodies and the blocking reagents to what classes the primary antibodies belong to. This makes the inventive labeling method much more versatile, for example when used in a multi-immunolabeling setting. Furthermore, the invention creates a much more stable immunolabeling complex than a complex between two antibodies. The high stability of the complex makes it comparable to a directly conjugated antibody using conventional conjugation chemistry.

The above description has been specifically exemplified in relation to the use of monovalent tetrameric streptavidin as a component of the monovalent biotin-binding composition being labeled with a reporter element. However, as is outlined above, it may in accordance to the invention be possible to allow the monovalent biotin-binding composition to be based on different monovalent biotin-binding molecules, such as for example monomeric streptavidin, avidin, traptavidin, captavidin, tamavidin, bradavidin, neutravidin, and rhizavidin, or any further developed or found equivalent molecule or combinations of molecules having an appropriate biotin-binding configuration.

Although the figures may show a specific order of method steps, the order of the steps may differ from what is depicted. Also two or more steps may be performed concurrently or with partial concurrence. Such variation will depend on designer choice. All such variations are within the scope of the disclosure. Additionally, even though the invention has been described with reference to specific exemplifying embodiments thereof, many different alterations, modifications and the like will become apparent for those skilled in the art. Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A method for forming an immunolabeling complex for use in contacting with a sample, wherein the method comprises:
    providing a biotinylated primary antibody comprising a primary antibody conjugated with a plurality of biotin molecules;
    providing a monovalent biotin-binding composition labeled with a reporter element, the monovalent biotin-binding composition comprising at least one of monovalent streptavidin or traptavidin, wherein the monovalent biotin-binding composition is conjugated with the reporter element, and wherein the reporter element comprises a fluorochrome;
    mixing, in a liquid phase in a reaction vessel, the biotinylated primary antibody with the labeled monovalent biotin-binding composition under conditions that form the immunolabeling complex; and
    adding a blocking agent to block unbound portions of the monovalent biotin-binding composition after the biotinylated primary antibody has formed a complex with the labeled monovalent biotin-binding composition to thereby form the immunolabeling complex, wherein the blocking agent comprises free biotin, and wherein the immunolabeling complex is a unit formed in absence of the sample.

2. The method according to claim 1, wherein mixing the biotinylated primary antibody with the first labeled monovalent biotin-binding composition attaches the reporter element to the biotinylated primary antibody.

3. The method according to claim 1, wherein the sample is different from the first biotinylated primary antibody.

4. The method according to claim 1, further comprising:
    providing an instruction to use the immunolabeling complex for immunolabeling of a sample.

5. The method according to claim 1, wherein providing the biotinylated primary antibody and providing the monovalent biotin-binding composition are performed separately from mixing the biotinylated primary antibody with the labeled monovalent biotin-binding composition.

6. The method according to claim 1, wherein the monovalent biotin-binding composition is modified to increase a number of conjugation sites to permit attachment of an increased number of reporter elements.

7. The method according to claim 1, wherein the monovalent biotin-binding composition is conjugated with macromolecules containing a plurality of molecules of the reporter element.

* * * * *